United States Patent
Keith et al.

(10) Patent No.: US 8,623,917 B2
(45) Date of Patent: Jan. 7, 2014

(54) USES OF PROSTACYCLIN ANALOGS

(75) Inventors: Robert L. Keith, Highlands Ranch, CO (US); Mark W. Geraci, Aurora, CO (US); York E. Miller, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 11/421,873

(22) Filed: Jun. 2, 2006

(65) Prior Publication Data

US 2006/0276546 A1      Dec. 7, 2006

Related U.S. Application Data

(60) Provisional application No. 60/687,016, filed on Jun. 2, 2005.

(51) Int. Cl.
*A61K 31/19*      (2006.01)

(52) U.S. Cl.
USPC ............................................. 514/557

(58) Field of Classification Search
None
See application file for complete search history.

(56) References Cited

U.S. PATENT DOCUMENTS

| | | | |
|---|---|---|---|
| 5,496,850 | A | 3/1996 | Mutoh et al. |
| 5,545,671 | A | 8/1996 | Schneider et al. |
| 7,276,490 | B1 | 10/2007 | Tanabe et al. |
| 2003/0108512 | A1 | 6/2003 | Shorr et al. |
| 2003/0166728 | A1* | 9/2003 | Shorr et al. |
| 2005/0085540 | A1 | 4/2005 | Phares et al. |

FOREIGN PATENT DOCUMENTS

| | | |
|---|---|---|
| WO | WO 03/072059 | 9/2003 |
| WO | WO 2004/017993 | 3/2004 |
| WO | WO 2006/008437 | 1/2006 |
| WO | WO 2008/088617 | 7/2008 |

OTHER PUBLICATIONS

Keith et al., "Manipulation of Pulmonary Prostacyclin Synthase Expression Prevents Murine Lung Cancer", 2002, Cancer Research, vol. 62, pp. 734-740.*
MedicineNet, "Cancer", downloaded from http://www.medterms.com/script/main/art.asp?articlekey=2580, accessed Apr. 7, 2008, pp. 1-2 of 2.*
Suggitt et al., "50 Years of Preclinical Anticancer Drug Screening: Empirical to Target-Driven Approaches", 2005, Clinical Cancer Research, vol. 11, pp. 971-981.*
Merriam-Webster OnLine Dictionary, "Prevent", downloaded fromhttp://www.merriam-webster.com/dictionary/prevent, accessed Apr. 7, 2008, pages 1 of 1.*
Winterhalder et al., "Chemoprevention of lung cancer—from biology to clinical reality", Annals of Oncology, Feb. 2004, vol. 15, pp. 185-196.*
Dresler, C., Lung Cancer, 2003, vol. 39, pp. 119-124.*
Kushiro et al., "Therapeutic Effects of Prostacyclin Analog on Crescentic glomerulonephritis of rat", Kidney International, 1998, v.53, pp. 1314-1320.
Naeije et al., "Pulmonary hypertension associated with COPD", Crit. Care, 2001, v.5(6), pp. 286-289.
Jones et al., "Pulmonary Vasodilation with prostacyclin in primary and secondary pulmonary hypertension", Chest, 1989, v.96, pp. 784-789.

* cited by examiner

*Primary Examiner* — Savitha Rao
*Assistant Examiner* — Gregg Polansky
(74) *Attorney, Agent, or Firm* — Don D. Cha; Hamilton DeSanctis & Cha, LLP

(57) ABSTRACT

The present invention provides a method for preventing or reducing the risk of cancer or the progression of premalignant dysplasia in a subject having a higher risk factor by administering a therapeutically effective amount of prostacyclin analog.

5 Claims, No Drawings

USES OF PROSTACYCLIN ANALOGS

CROSS-REFERENCE TO RELATED APPLICATIONS

This application claims the priority benefit of U.S. Provisional Application No. 60/687,016, filed Jun. 2, 2005, which is incorporated herein by reference in its entirety.

STATEMENT REGARDING FEDERALLY FUNDED RESEARCH

This invention was made with government support under grant numbers CA58187 and CA70907 awarded by the National Institutes of Health. The government has certain rights in the invention.

FIELD OF THE INVENTION

The present invention relates to uses of prostacyclin analogs including, but not limited to, reducing the risk of developing cancer or the progression of premalignant dysplasia.

BACKGROUND OF THE INVENTION

Cancer is one of the leading causes of death. In particular, lung cancer is the number one cause of cancer death in men and women not only in the United States but worldwide. Lung cancer is a medical priority due to the high rates of tobacco addiction and exposure to tobacco products in the general population. Additionally, lung cancer occurs in subjects exposed to chemicals, such as Agent Orange, and other carcinogens such as coal dust, asbestos, and radiation.

Even if all current smokers were to abstain from tobacco, lung cancer would remain an epidemic for many years. In fact, the majority of lung cancers are now diagnosed in former smokers. Currently, there are no established screening tests for the early detection of lung cancer, and less than 25% of patients present with surgically curable disease. The cumulative five-year survival rate for lung cancer is approximately only 15%. Because the survival rate is so low, it would be more effective to prevent lung cancer from developing rather than trying to treat it after the subject has developed lung cancer.

SUMMARY OF THE INVENTION

In one aspect, the present invention provides a method of reducing a subject's risk of developing cancer. This method is particularly useful in a subject having a higher risk factor for developing cancer relative to a person not having a similar risk factor. The method comprises administering a therapeutically effective amount of a prostacyclin analog to the subject. In this manner, a variety of cancers including, but not limited to, lung, liver, brain, pancreatic, kidney, prostate, breast colon, bladder, ovarian and head and-neck cancer may be prevented. Typically, at least about 10 percent of the risk of developing cancer is reduced in the subject having the high risk factor.

Another aspect of the present invention provides a method for reducing the risk of developing advanced premalignant dysplasia in a subject.

DETAILED DESCRIPTION OF THE INVENTION

With the rising costs of healthcare and the rising incidence of cancer, healthcare providers are in need of an easily administered approach to the prevention of cancer. If cancer onset could be hindered or prevented, then treatments such as chemotherapy as a result of the disease would be avoided. Some chemoprotection or chemoprevention efforts have focused on dietary factors such as vitamins and micronutrients. Although vitamin supplements may prevent or reduce the risk of cancer, in some studies the opposite was found. Some researchers also have found a negative correlation between a diet high in fruits and vegetables and lung cancer incidence. For example, β-carotene is generally believed to have positive effects on reducing cancer incidence; however, one study showed increased lung cancer in humans. Another study in animals appeared to show that both vitamin A and β-carotene supplement increases pulmonary adenomas. With these seemingly conflicting results it is apparent other effective approaches are needed to prevent the development of cancer.

Lung cancer is a significant health problem in the US and is the number one cause of cancer death in both men and women in both the US and worldwide. It is believed that approximately 160,000 deaths occur per year due to lung cancer. More than half of these lung cancer cases are in former smokers.

In one aspect, the present invention provides methods for reducing the risk of developing or preventing incidence of cancer in a subject. Methods of the present invention are suitable for, but not limited to, reducing the risk of developing lung, liver, brain, pancreatic, kidney, prostate, breast, colon, or head-neck cancer. In one specific embodiment, methods of the present invention are used to reduce the risk of developing lung cancer. Typically, methods of the present invention include administering a therapeutically effective amount of a prostacyclin analog to a subject having a high risk factor.

"Reducing the risk" in developing cancer refers to decreasing the probability of a subject developing a cancer relative to a control group having a similar high risk factor but is untreated with prostacyclin analog or treated with placebo. One skilled in the art can readily determine the effectiveness of risk reduction. Such analysis typically requires a case-control study where some members of the group (case group) having a high risk of developing cancer are treated with prostacyclin analog while other members within the same group (control group) are not treated or are given placebo. To determine the effectiveness of a prostacyclin analog in reducing the incidence (or risk) of cancer development, the case-control groups are observed for a period of time that is deemed to be sufficient to provide a statistically significant analysis. As will be appreciated, the number of subjects in the case-control should be sufficient in number in order to provide a statistically significant result. In addition, animal model studies can be used to determine the effectiveness of prostacyclin analog to reduce the cancer risk.

Decrease in the risk is typically determined by comparing the differences in the incidence of cancer development or progression of pre-malignant dysplasia between the control group and the case group after a certain period of time. Comparisons may include but are not limited to comparing tissue samples, cell samples, sputum samples, x-rays, blood samples and the like. Any known method for comparison of these types of cell samples may be used to assess the relative change in the risk of developing the cancer.

As used herein, a "high risk factor" refers a factor that increases the likelihood of a subject developing cancer. Exemplary high risk factors include, but are not limited to, environmental factors, predisposed genetic factor, exposure to tobacco products, exposure to chemicals, radiation or asbestos, and other factors that are known to increase the risk of various cancers. For example, smokers are at a higher risk in developing lung cancer compared to non-smokers. In one particular embodiment, the high risk factor refers to a subject who has been smoking at least ½ to one pack of cigarettes per day for at least 1 year, preferably at least 3 years, more preferably at least 5 years, still more preferably at least 10 years, and most preferably at least 20 years. For the sake of brevity and clarity, the present invention will now be illustrated in reference to cigarette smoke exposure as the high risk factor; however, it should be appreciated that the scope of the present invention includes other high risk factors, such as those disclosed above.

Typically, methods of the present invention decrease or reduce the risk of developing cancer in the subject by at least 10% relative to a control group with the similar risk factor. Preferably, the risk is reduced by at least 15%, more preferably by at least 20%, and most preferably by at least 30%.

Prostacyclin analog refers to a compound, or a pharmaceutically acceptable salt thereof that acts in a similar manner as prostacyclin (prostaglandin $I_2$, $PGI_2$). In particular, prostacyclin analog refers to a compound that mimics the in vivo action of $PGI_2$ or modulates the same enzyme as $PGI_2$. There are a variety of in vitro assay methods available to determine whether a particular compound maybe considered as a prostacyclin analog. Any known prostacyclin analogs that are currently available may be used in methods of the present invention. In one particular embodiment, the prostacyclin analog is selected from Iloprost, Beraprost, treprostenil (Remodulin®), and a combination thereof. A particularly preferred prostacyclin analog is Iloprost. Interestingly, it has been found that administering Iloprost to mice did not prevent cancer metastasis to the lung. See, for example, U.S. Pat. No. 5,545,671. However, unlike the previous study, the present invention is directed to preventing cancer from developing in the first place not preventing metastasis.

Iloprost is a synthetic analogue of prostacyclin ($PGI_2$) which is chemically stable and has a longer half-life than the naturally occurring substance. Iloprost is manufactured by Schering AG (Berlex Laboratories in the US). It can be administered orally, parenterally, or by inhalation. Iloprost is available for oral administration as Iloprost acid, Iloprost sodium, and Iloprost clathrate and, immediate-release tablets and capsules, and extended-release capsules.

Methods of the present invention may also be used to reduce a progression of premalignant dysplasia in a subject having a high risk factor for developing premalignant dysplasia relative to a person not having a similar risk factor.

Prostacyclin analogs may be administered in combination with other therapeutically useful agents, such as a cyclooxygenase (COX) inhibitor, and peroxisome proliferator-activated receptor (PPAR) γ agonists (e.g., thiazolidinediones such as rosiglitazone pioglitazone, and ciglitazone).

Formulations

Prostacyclin analogs can be administered to a subject to achieve a desired physiological effect. Preferably the subject is an animal, more preferably a mammal, and most preferably a human. The Prostacyclin analog can be administered in a variety of forms adapted to the chosen route of administration, e.g., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The prostacyclin analog can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the prostacyclin analog may be incorporated with excipient and used in the form of ingestible tablets, buccal tablets, troches, capsules, elixirs, suspensions, syrups, wafers, and the like. Such compositions and preparation can contain at least 0.1% of active prostacyclin analog. The percentage of the compositions and preparation can, of course, be varied and can conveniently be between about 1 to about 10% of the weight of the unit. The amount of active prostacyclin analog in such therapeutically useful compositions is such that a suitable dosage will be obtained. Preferred compositions or preparations according to the present invention are prepared such that an oral dosage unit form contains from about 1 to about 1000 mg of active prostacyclin analog. In one particular embodiment, prostacyclin analog is administered orally or by an aerosol delivery system.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the prostacyclin analog, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the prostacyclin analog can be incorporated into sustained-release preparations and formulation.

The prostacyclin analog can also be administered parenterally. Solutions of the prostacyclin analog can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the prostacyclin analog in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The prostacyclin analog can be administered to a mammal alone or in combination with pharmaceutically acceptable carriers, as noted above, the proportion of which is determined by the solubility and chemical nature of the prostacyclin analog, chosen route of administration and standard pharmaceutical practice.

The physician will determine the dosage of the prostacyclin analog which will be most suitable for prophylaxis or treatment and it will vary with the form of administration and the particular prostacyclin analog chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. Procedures that are constructively reduced to practice are described in the present tense, and procedures that have been carried out in the laboratory are set forth in the past tense.

EXAMPLES

About 20% of lung cancers are small cell lung cancer (SCLC). These are the most aggressive and rapidly growing of all lung cancers. SCLC correlates strongly to cigarette smoking with only 1% of these tumors occurring in non-smokers. SCLC metastasizes rapidly to many sites within the body and are most often discovered after they have spread extensively. Referring to a specific cell type often seen in SCLC, these cancers are sometimes called oat cell carcinomas.

Non-small cell lung cancer (NSCLC) are the most common lung cancers, accounting for about 80% of all lung cancers. NSCLC has three main types that are named based upon the type of cells found in the tumor namely adenocarcinoma, squamous cell carcinoma and large cell carcinomas.

Adenocarcinomas are the most commonly seen type of NSCLC in the U.S. and include about 50% of NSCLC. While adenocarcinomas are associated with smoking like other lung cancers, this type is especially observed in non-smokers who develop lung cancer. Most adenocarcinomas arise in the outer, or peripheral, areas of the lungs. Bronchioloalveolar carcinoma is a subtype of adenocarcinoma that frequently develops at multiple sites in the lungs and spreads along the preexisting alveolar walls. Squamous cell carcinomas were formerly more common than adenocarcinomas; at present they account for about 30% of NSCLC. Also known as epidermoid carcinomas, squamous cell cancers arise most frequently in the central chest area in the bronchi and are strongly associated with tobacco smoke exposure.

Large cell carcinomas, sometimes referred to as undifferentiated carcinomas, are the least common type of NSCLC. Mixtures of different types of NSCLC are also seen. Other types of cancers can arise in the lung. These types are much less common than NSCLC and SCLC including about 5-10% of lung cancers.

Tobacco smoking is the major risk factor for lung cancer. Airflow obstruction, chronic bronchitis or chronic obstructive pulmonary disease (COPD) occurs in approximately 25% of smokers. This subgroup has a significantly increased incidence of lung cancer, compared to smokers with similar smoking histories but no airflow obstruction. A subject having airflow obstruction, chronic bronchitis or COPD with an increased risk of developing lung cancer can be treated with a prostacyclin analog and compared to a control subject with the similar airflow obstruction, chronic bronchitis or COPD to assess the reduction in risk of developing lung cancer.

Exposure to chemical substances can cause adverse effects on the respiratory system, which consists of the nasal passages, pharynx, trachea, bronchi, and lungs. Respiratory toxicity can include a variety of acute and chronic pulmonary conditions, including local irritation, bronchitis, pulmonary edema, emphysema, and cancer. It is well known that exposure to environmental and industrial chemicals can impair respiratory function including causing lung cancer. Ground-level ozone, the main component in smog, causes breathing problems, aggravates asthma, and increases the severity and incidence of respiratory infections. Acute exposure to respiratory toxicants can trigger effects ranging from mild irritation to death by asphyxiation. Prolonged exposure to respiratory toxicants can cause structural damage to the lungs, resulting in chronic diseases such as pulmonary fibrosis, emphysema, and cancer. Pulmonary fibrosis is a serious lung disease in which airways become restricted or inflamed, leading to difficulty in breathing. It can be caused by exposure to coal dust, aluminum, beryllium, and carbides of tungsten.

Emphysema, a degenerative and potentially fatal disease, is characterized by the inability of the lungs to fully expand and contract. The most common cause of emphysema is heavy cigarette smoking, but the disease can also be induced by exposure to aluminum, cadmium oxide, ozone, and nitrogen oxides. In addition, several toxicants are known to cause respiratory cancer. Examples of well-established human lung carcinogens are cigarette smoke, asbestos, arsenic, and nickel. Cigarette smoke contains more than 4,000 different chemicals, many of which are proven cancer-causing substances, or carcinogens. Smoking cigars or pipes also increases the risk of lung cancer.

Radon is believed to be the second leading cause of lung cancer in the U.S. today. Radon gas can come up through the soil under a home or building and enter through gaps and cracks in the foundation or insulation, as well as through pipes, drains, walls or other openings. Radon causes a significant number of lung cancer deaths each year in the United States. Radon problems have been found in every state. Radon can be a problem in schools and workplaces, too. Exposure to radon in combination with cigarette smoking greatly increases the risk of lung cancer. That means for smokers, exposure to radon is an even greater health risk.

Another leading cause of lung cancer is on-the-job exposure to cancer-causing substances or carcinogens. Asbestos is a well-known, work-related substance that can cause lung cancer, but there are many others, including uranium, arsenic, and certain petroleum products. There are many different jobs that may involve exposure. Some examples are working with certain types of insulation, working in coke ovens, and repairing brakes. When exposure to job-related carcinogens is combined with smoking, the risk of getting lung cancer is sharply increased. Lung cancer takes many years to develop, but changes in the lung can begin almost as soon as a person is exposed to cancer-causing substances.

Occupational exposure to bis-chloromethyl ether and radon preferentially influence small cell carcinoma. With regard to diet, some positive associations have been seen with lipid consumption, fat and cholesterol, and inverse associations with various carotenoids, vitamin C, and retinol, and with fruits and vegetables as a group. Immunologic and hormonal factors have also been suggested to affect risk of adenocarcinoma.

Chemoprevention of Murine Lung Carcinogenesis

Transgenic mice with pulmonary prostacyclin synthase (PGIS) overexpression were created using a construct of the human surfactant protein C (SPC) promoter and the rat PGIS cDNA. The human SPC promoter is believed to direct expression of transgenes to alveolar type II and Clara cells, which are believed to be the progenitors for human and mouse lung adenocarcinomas. To determine a gene-dosing effect, two different transgenic lines were developed and exposed to carcinogens, low expressing mice with a 50% increase in lung PGIS activity (exhibited by a 1.5-fold increase in $PGI_2$ compared to wildtype littermates) and a high expressing line with a 3-fold increase in lung $PGI_2$.

Transgenic mice ($Tg^+$) and wildtype littermates ($Tg^-$), 8 to 12 weeks of age, were subjected to two distinct lung carcinogenesis protocols. In the first model, urethane (ethyl carbamate), a carcinogen which selectively induces pulmonary adenomas through genetic mutations in the oncogene ras, was administered in a single intraperitoneal (ip) dose. In an initiation/promotion model, 3-methylcholanthrene (MCA), a polycyclic aromatic hydrocarbon found in tobacco smoke which exhibits dose-dependent initiation of murine lung tumors, was given as a single ip dose, followed by six weekly ip treatments with butylated hydroxytoluene (BHT). BHT is a tumor promoter and induces reversible pulmonary damage characterized by alveolar type I cell necrosis, selective pulmonary inflammation, and hyperplasia of alveolar type II cells. Controls for both models consisted of mice injected with vehicle alone.

Transgenic overexpression of PGIS significantly decreased tumor multiplicity and incidence in both carcinogenesis models. $Tg^+$ mice expressing low levels of PGIS exhibited a 50% reduction in urethane-induced tumor multiplicity (3.4 vs. 6.8 tumors/mouse, $p<0.001$) and a 66% reduction in the MCA/BHT model (2.5 vs. 7.5 tumors/mouse, $p<0.001$). Untreated mice failed to develop tumors. $Tg^+$ mice expressing high levels of PGIS exhibited even greater chemoprotection, demonstrating an 85% reduction in tumor multiplicity compared to $Tg^-$ littermates (0.8 vs. 5.2 tumors/mouse, $p<0.0001$). Lung tumor incidence was also decreased in these high-expressing mice, with 44% (8/18) of the $Tg^+$ mice remaining tumor free as compared to the 100% incidence in $Tg^-$ littermates ($p=0.01$, Fisher's exact test).

Chemoprevention in a Tobacco Smoke Exposure Model

Murine exposure to tobacco smoke as an established model of inducing pulmonary adenocarcinomas can be used. It is believed that this lung carcinogenesis model closely parallels the human disease. PGIS overexpressors were exposed to mainstream cigarette smoke for 22 weeks and then held unexposed for an additional 20 weeks. $Tg^+$ mice, when compared to smoke-exposed $Tg^-$ littermates, had significant decreases in tumor incidence and multiplicity. Significantly fewer transgenics (6/15, 40%) developed tumors compared to the tumor incidence in wildtype littermates (16/19, 84%) (Fisher's exact test, $p=0.012$). Tumor multiplicity was also significantly decreased in the transgenic animals ($tg^+$=0.4+/−0.5 vs. wt=1.2+/−0.86 tumors/mouse, $p<0.001$).

Protection by PGIS overexpression in these distinct carcinogenesis models demonstrates the generality of the chemoprevention. These studies illustrate that manipulation of prostaglandin metabolism distal to COX produces more profound lung cancer reduction than COX inhibition alone.

Elevated $PGI_2$ Levels

Baseline 6-keto $PGF_{1\alpha}$ (the stable breakdown product of $PGI_2$) levels were determined for $Tg^+$ animals, and at the termination of both carcinogenesis protocols, simultaneous 6-keto $PGF_{1\alpha}$ and $PGE_2$ levels were measured. In both carcinogenesis models, the significant elevations in 6-keto $PGF_{1\alpha}$ over baseline persisted at the time of sacrifice, whereas decreased $PGE_2$ levels were not observed in the MCA/BHT model. In the many carcinogenesis models applied to the PGIS overexpressors, elevation of $PGI_2$ (not decreases in $PGE_2$) was observed for chemoprevention to occur.

Lung Tumorigenesis Prevention

The oral administration of Iloprost was investigated and found to have a similar beneficial effects to PGIS overexpression. FVB/N mice were fed a diet of low (0.1%) or high (3.0%) dose Iloprost continuously throughout the experiment and then were subjected to tumorigenesis protocols with either urethane or MCA/BHT. At the conclusion of the experiments, animals were euthanized and tumors enumerated. Animals in both carcinogenesis protocols had a significant reduction in tumor multiplicity. There was a greater reduction in multiplicity observed with 3.0% Iloprost.

Chemoprevention Study of Iloprost in Patients at High Risk for Lung Cancer

Iloprost is a long-acting, orally available prostacyclin analogue. The long-term safety of oral Iloprost has been established in subjects with various conditions, including primary pulmonary hypertension, scleroderma with Raynaud's phenomenon, peripheral vascular disease/atherosclerosis with lower extremity ulceration, and Buerger's disease (thromboangiitis obliterans) who have received the drug for 6 months or longer.

Squamous cell carcinoma of the lung (SCC) is one of the four major subtypes of lung cancer, and is the second most common form of NSCLC to adenocarcinoma. SCC typically arises from the central airways (including the trachea, mainstream bronchi and subsegmental bronchi), and histological/cytological studies have clearly shown a series of predictable pathologic changes that can eventually progress to bronchogenic carcinoma. Fluorescent bronchoscopy can be utilized to detect bronchial epithelial lesions. Fluorescent bronchoscopy relies on autofluorescence to detect premalignant lesions in the central airways. LIFE (Laser Induced Fluorescence Endoscopy) was developed to improve detection of premalignant dysplasia. Dysplastic lesions are less reliably visualized during white light bronchoscopy. LIFE bronchoscopy has approximately a six-fold increase in sensitivity for detecting moderate or greater dysplasia, compared to white-light bronchoscopy. LIFE bronchoscopy is the preferred modality for detecting angiogenic squamous dysplasia (ASD), a central airway lesion characterized by capillary blood vessels projecting into metaplastic or dysplastic squamous bronchial epithelium. The studies regarding the natural history of ASD suggest it may occur more often in patients who develop squamous cell lung cancer.

The trial consists of Iloprost or placebo administered to patients at high risk for lung cancer (based on sputum cytologic atypia and pack years) in a double blind, randomized prospective trial of six months duration. Eligible patients are randomly assigned to active treatment or placebo treatment within each stratum. Measurement of response includes: pre and post treatment histology using the World Health Organization (WHO) classification for bronchial epithelium (primary endpoint); Ki-67 labeling index (secondary endpoint); and a panel of biomarkers (including immunohistochemistry and quantitative polymerase chain reaction (qPCR) for PGIS, COX-2, PPAR δ, PPAR γ, MCM2, p53, tyrosine kinase receptor proteins [EGFR, HER2/neu, ErbB3, ErbB4, Akt], and microvessel density by CD-31 staining).

In vitro Assay Method

Prostacyclin analogs can be administered to cells such as cultured squamous cell lung cancer cell lines to test the inhibitory properties of prostacyclin analogs. In another exemplary method, prostacyclin analogs may be administered to mice to assess the chemoprevention capabilities against a potential cancer such as lung carcinogenesis development in the described murine model of squamous cell lung cancer. The results of these studies can be used to assess the efficacy of a prostacyclin analog alone or in combination with other treatments to inhibit the development of a cancer in a subject such as an animal or human subject.

Protective Effect of PGIS Overexpression

To define the effect of the prostacyclin membrane receptor on chemoprevention, bi-transgenic mice were generated. First, mice with targeted disruption of the prostacyclin receptor (PGIR) were backcrossed ten generations into the FVB/N strain in order to be congenic with the PGIS Tg+ animals. A series of crosses was then performed to generate bi-transgenic animals (i.e., a PGIS overexpressing PGIR knockout animal). In this strategy, the contribution of signaling through the PGIR could be determined. Animals were then subjected to the urethane carcinogenesis protocol. The chemoprevention was independent of the PGIR. Animals with PGIR −/− or PGIR −/+ had the same tumor multiplicity as wild types. Furthermore, the PGIS transgene protected even in the absence of the PGIR. Without being bound by any theory, it is believed that this observation suggests that chemoprevention is independent of the cell membrane $PGI_2$ receptor.

Chemoprevention of Cancer and Reduce Pre-Malignant Bronchial Dysplasia

Mouse lung tumorigenesis models are dependent on murine strain, and a large number of strains were evaluated with the NTCU model. FVB mice, the strain of genetically modified mice, were tested and classified as 'intermediately susceptible' based on the incidence of: Squamous cell carcinoma of the lung (SCC) (4/9, 44%); SCC in situ (7/9, 78%); bronchiolar metaplasia (9/9, 100%); and bronchioloar hyperplasia (8/9, 89%). This mimics the various pathologic lesions found in the airways of current and former smokers. Therefore, this model of SCC allows for the evaluation of PGIS overexpression and/or Iloprost efficacy in the occurrence of both SCC and pre-malignant bronchial dysplasia.

To determine if prostacyclin can alter the development of premalignant murine lesions and murine SCC, one exemplary method is to apply the NTCU model to FVB/N PGIS overexpressors and wildtype FVB/N mice receiving oral Iloprost. Iloprost treatment is begun one week prior to initiation of the carcinogenesis protocol and continued throughout the experiment.

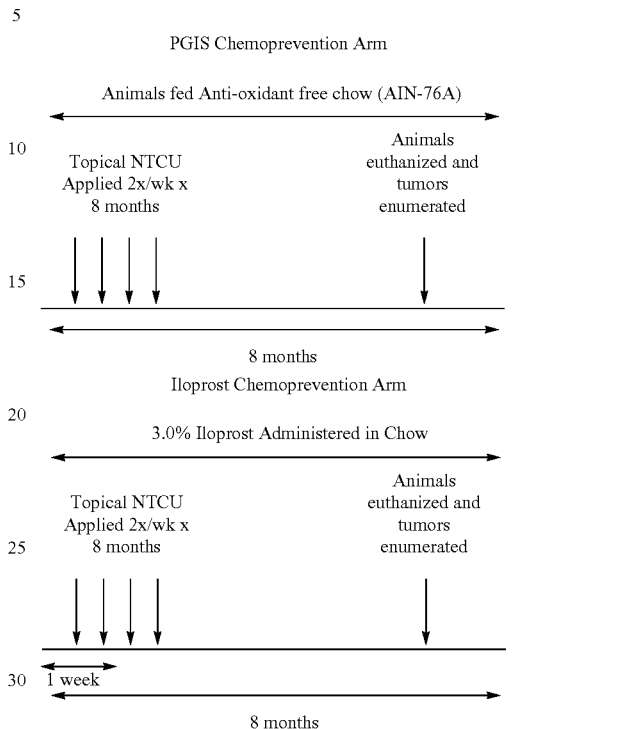

The experimental groups (with 20 FVB/N mice/group) are:
1. PGIS Overexpressors treated with NTCU
2. PGIS Overexpressors treated with acetone (the delivery vehicle for NTCU)
3. Wildtype Littermates treated with NTCU
4. Wildtype littermates treated with acetone
5. Wildtype animals receiving 3.0% Iloprost chow treated with NTCU
6. Wildtype animals receiving control chow treated with NTCU The experimental scheme is outlined as follows: NTCU SCC model: The dorsal skin of 8-10 week old animals is shaved 48 hours before the initial treatment. One group of mice is treated with topical NTCU: 25 μl drop of 0.04M, twice a week with a 3 day interval between treatments. The control animals are treated with one drop of acetone (the solvent used to dissolve the NTCU). Eight months after the initial treatment with NTCU the animals are euthanized by pentobarbital overdose and the lungs are harvested for determination of tumor incidence, multiplicity, and the presence of SCC in situ and bronchial dysplasia. Both tumor and surrounding lung are preserved in 10% formalin for routine H&E staining. Serial sections (5 μm each) are made from formalin fixed tissue, and 1 in every 20 sections are stained with H&E and examined with light microscopy. Additional specimens of tumor and surrounding lung are either flash frozen in liquid nitrogen and stored for future DNA and protein analysis, or placed in an RNA preserving solution (RNAlater) for potential gene expression studies in the future.

For the carcinogenesis protocols, a sample size of 20 animals is determined for an alpha=0.05 significance level using a two-tailed independent sample T-test. Power analysis reveals a >90% chance of detecting significant differences in tumor numbers by including 20 mice in each experimental group. The data are subjected to unpaired t-tests and Pearson tests (tumor number, tumor volume) to confirm significance. Statistical significance of differences in tumor number are tested by a Student's T-test. The power to detect an increase in tumor number from 5 to 6 in one group is calculated compared to the other at a p value of 0.05, with standard deviations of 1 in each group and group size of 20 to be 0.86.

Growth Fraction

A common endpoint of pathways affected by Iloprost is cell proliferation. Ki-67 labeling is an indicator of proliferative index and can be readily detected in bronchial biopsy material. Ki-67 labeling scores increase with grade of bronchial dysplasia with a mean of 4% in normal and hyperplastic samples which increases to 38% in biopsies with moderate or severe dysplasia. See Table 1. Furthermore, current smokers have higher Ki-67 labeling score (mean 31%) as compared to former smokers (mean 18%). When a serial set of matched biopsies were examined for change over time there was correlation between histological change and Ki-67 labeling scores. Accordingly, one method for assessing a reduced risk of developing cancer in a therapeutically treated subject is to analyze the Ki-67 growth fraction.

TABLE 1

Histology in Bronchial Epithelium of High Risk Subjects

|  | Histology | Ki-67(mean %) |
|---|---|---|
| Study Population | Grade 1-2 (N = 14 biopsies) | 4% |
|  | Grade 3-4 (N = 16 biopsies) | 20% |
|  | Grade 5-6 (N = 39 biopsies) | 38% |
| Current Smokers (N = 11) | Mean grade 4.4 | 31% |
| Former Smokers (N = 5) | Mean grade 3.0 | 18% |
| Serial Biopsies: |  |  |
| No change (N = 7) | Mean grade change 0 | −17% |
| Progression (N = 10) | Mean grade change +2 | +17% |
| Improvement (N = 4) | Mean grade change −2.5 | −21% |

Ki-67 thus is an easily performed proliferative index that is a primary endpoint in this study.

Cell Attachment and Proliferation

Equal numbers of cells are plated in 96 well plates (5000/well). At various times, plates are rinsed with Hanks, and cell attachment quantitated by MTT cell viability assay. Initial studies are done using uncoated standard tissue culture dishes. Attachment to specific extracellular matrices is examined. Dishes are coated with Type I collagen, fibronectin, or Matrigel, and attachment determined. Growth is measured as changes in cell number under standard tissue culture conditions (cells plated on plastic dishes) as a function of time. Experiments are performed in full media [10% fetal calf serum (FCS)], as well as in growth factor depleted media to determine autonomous growth. Plates are assayed for live cells 72 hrs later by the CellTiter 96 Aqueous One Solution Cell Proliferation Assay (Promega; MTT Assay). Results are calculated as percentage of live cells.

Migration

Cell migration are measured using Transwell assays in a fibronectin motility assay. Insert containing 8 µm pores (Falcon) is coated with fibronectin in 24 well plates using 30 µl of a 10 µg/ml stock. Equal numbers (~30,000) of each NSCLC cell stably overexpressing either PPAR γ, PGIS or empty vector are plated on the transwells and incubated for varying lengths of time. At each time point, the transwells are removed, fixed in 4% paraformaldehyde. Cells attached to the top of the transwell are removed with a cotton swab, and cells on the bottom of the transwell are stained with Crystal Violet. Migrating cells are quantitated by counting at least 3 independent fields/well. In initial experiments the bottom of the transwell contains media with 0.5% FCS. Iloprost is added to the bottom chamber at increasing concentrations (starting at 1 µM and increasing to 5 µM).

Invasion

Cell invasion into Matrigel is determined using the Matrigel invasion chamber assay (BD Biosciences). In this assay cells are plated on Transwells which have been coated with Matrigel, or Transwells coated with bovine serum albumin (BSA) (control). Cell quantitation is performed as described for the migration assays. For each cell line the % invasion is calculated as the fraction of cells migrating through the Matrigel membrane divided by cells migrating through the control membrane. For cells overexpressing PPAR γ or PGIS, an invasion index is then calculated as the % invasion of cells overexpressing PPAR/% invasion of cells transfected with empty vector.

Scratch Assay

As an alternative to the Transwell Migration assay, cell migration can be examined by the ability of cells to fill in a scratch on a culture dish. Cells are grown to confluence, and allowed to become quiescent by incubation in media without FCS. A 30-100 µm scratch is made in the culture using a pipet tip. The ability of cells to fill the gap created by the pipet tip is determined as a function of time by taking pictures of the same field of cells. If there are significant differences in the rate of attachment of cells overexpressing PPAR γ or PGIS, results of the Transwell assay reflect both differences in attachment and migration, making interpretation more difficult.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for reducing a risk of developing lung cancer in a human former smoker, said method comprising administering a therapeutically effective amount of prostacyclin analog comprising iloprost to the former smoker such that the risk of developing lung cancer in the former smoker is decreased by at least 10% relative to a control group with the similar risk factor.

2. The method of claim 1, wherein the former smoker averaged at least 1 pack of cigarettes per day for at least 5 years.

3. The method of claim 1, wherein the risk of developing cancer in the subject is decreased by at least 20% relative to the control group.

4. A method for reducing a risk of developing premalignant lung dysplasia in a human former smoker, said method comprising administering a therapeutically effective amount of prostacyclin analog comprising iloprost to the former smoker such that the risk of premalignant lung dysplasia progression in the former smoker is decreased by at least 10% relative to a control group with the similar risk factor.

5. The method of claim 4, wherein the progression of premalignant dysplasia in the former smoker is decreased by at least 20% relative to the control group.

* * * * *